(12) United States Patent
Borom (10) Patent No.: US 6,984,066 B2
(45) Date of Patent: Jan. 10, 2006

(54) ATTACHABLE SURGICAL TABLE

(76) Inventor: Andrew H. Borom, 3656 Unlle Glover Rd., Tallahassee, FL (US) 32312

( * ) Notice: Subject to any disclaimer, the term of this patent is extended or adjusted under 35 U.S.C. 154(b) by 88 days.

(21) Appl. No.: 10/647,627

(22) Filed: Aug. 25, 2003

(65) Prior Publication Data

US 2005/0047554 A1    Mar. 3, 2005

(51) Int. Cl.
*A61B 6/04*     (2006.01)
*A61G 13/00*    (2006.01)

(52) U.S. Cl. .......................... 378/209; 378/208; 5/601; 108/42; 108/43; 108/97; 108/98

(58) Field of Classification Search ................ 378/167, 378/177–180, 189, 190, 193, 195–198, 208, 378/209; 5/601; 600/407, 425; 108/42, 108/43, 97, 98
See application file for complete search history.

(56) References Cited

U.S. PATENT DOCUMENTS

| 3,715,587 A | | 2/1973 | Burkhalter | |
|---|---|---|---|---|
| 4,649,560 A | * | 3/1987 | Grady et al. | ................ 378/196 |
| 4,653,083 A | * | 3/1987 | Rossi | .......................... 378/196 |
| 5,001,739 A | | 3/1991 | Fischer | |
| 5,018,176 A | * | 5/1991 | Romeas et al. | ................ 378/37 |
| 5,086,448 A | * | 2/1992 | Muthmann | .................. 378/197 |
| 5,490,524 A | | 2/1996 | Williams et al. | |
| 5,515,415 A | | 5/1996 | Herrmann et al. | |
| 5,802,719 A | | 9/1998 | O'Farrell, Jr. et al. | |
| 5,822,814 A | | 10/1998 | Van der Ende | |
| 6,095,685 A | * | 8/2000 | Tamura | ...................... 378/196 |
| 6,113,265 A | | 9/2000 | Babler | |
| 6,220,752 B1 | * | 4/2001 | Csikos et al. | ............... 378/197 |
| 6,256,374 B1 | | 7/2001 | Tomasetti et al. | |
| 6,285,902 B1 | | 9/2001 | Kienzle, III et al. | |
| 6,322,251 B1 | | 11/2001 | Ballhaus et al. | |
| 6,382,832 B1 | * | 5/2002 | Schwieker et al. | ......... 378/196 |
| 6,448,571 B1 | | 9/2002 | Goldstein | |
| 6,669,365 B2 | * | 12/2003 | Iinuma | ....................... 378/195 |

* cited by examiner

*Primary Examiner*—Allen C. Ho
(74) *Attorney, Agent, or Firm*—J. Wiley Horton (57) ABSTRACT

A small surgical table which can be attached directly to a C-arm X-ray machine. A flat plate of X-ray transparent material is provided as a surface on which surgical procedures can be performed. Clamping features are provided on the underside of this plate to allow its attachment to an image intensifier or an emitter of a C-arm machine. The clamping features are preferably made readily adjustable in order to allow the attachment of the surgical table to a wide variety of X-ray machines. The invention is particularly suited for surgeries involving a small portion of the anatomy—such as the hand. The direct attachment of the surgical table to the X-ray machine allows the surgeon to conveniently visualize the internal placement of orthopaedic hardware and other features both before and during the surgery.

12 Claims, 12 Drawing Sheets

ATTACHABLE SURGICAL TABLE

BACKGROUND OF THE INVENTION

1. Field of the Invention

This invention relates to the field of medicine. More specifically, the invention comprises a surgical table which can be attached directly to a common type of X-ray machine.

2. Description of the Related Art

Figure 1:
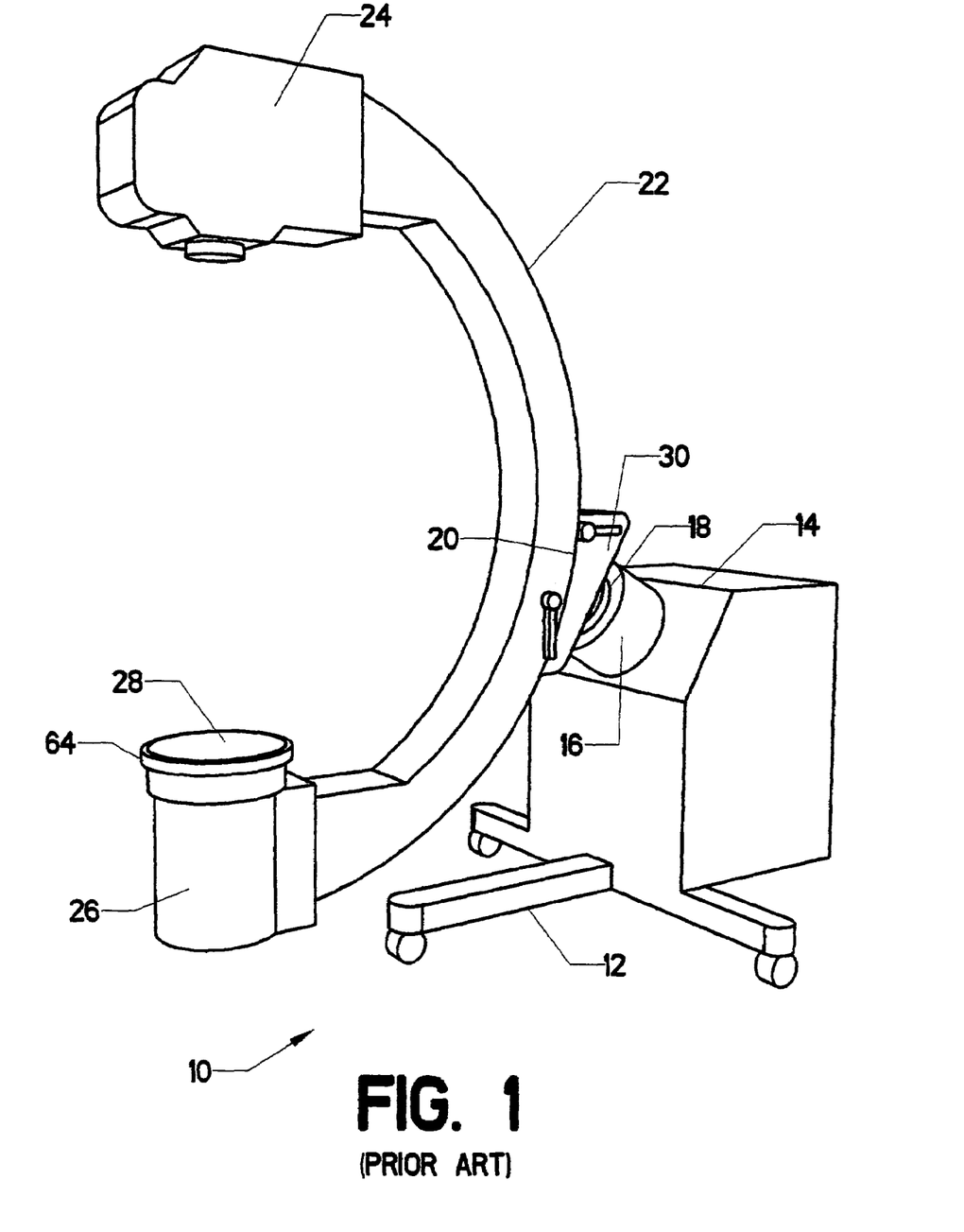
FIG. 1 is an isometric view, showing a prior art C-arm X-ray machine.

X-ray machines have been used in the practice of medicine for many decades. One such machine in common use is referred to as a "C-arm" machine. FIG. 1 depicts one example of such a machine. Those skilled in the art will know that a wide variety of such machines are in use. They generally share the same major components, however.

C-arm machine 10 is supported by base 12, which is typically furnished with lockable castors so that the machine can be easily moved to a desired location and fixed. Main housing 14 attaches to the base. This element provides structural support and also often houses the necessary electronic equipment. Sliding joint support 16 protrudes upward and forward from main housing 14. Pivot joint 18 rotatably attaches C-arm support 30 to sliding joint support 16. C-arm 22 is slidably attached to sliding joint support 16 by sliding joint 20. In the particular type of machine illustrated, pivot joint 18 and sliding joint 20 can be adjusted as desired—then locked into position.

The reader should be aware that not all C-arm machines have the adjustment features described. Simpler machines may be fixed in the position shown. The invention described hereinafter typically employs the C-arm machine in the position shown. Thus, the various adjustment features which a particular machine may possess are not significant to the present invention.

C-arm machine 10, like most X-ray devices, includes an emitter 24 and image intensifier 26. Though a discussion of X-ray machine technology is beyond the scope of this disclosure, those skilled in the art will know that emitter 24 generates X-rays and image intensifier 26 is generally configured to receive these rays and provide a useable image. Those skilled in the art will also know that the position of emitter 24 and image intensifier 26 may be reversed. Some image intensifiers 26 include a lip 64, which may assume the form of a gripping handle.

BRIEF SUMMARY OF THE INVENTION

The present invention comprises a small surgical table which can be attached directly to a C-arm X-ray machine. A flat plate of X-ray transparent material is provided as a surface on which surgical procedures can be performed. Clamping features are provided on the underside of this plate to allow its attachment to an image intensifier or an emitter of a C-arm machine. The clamping features are preferably made readily adjustable in order to allow the attachment of the surgical table to a wide variety of X-ray machines.

The invention is particularly suited for surgeries involving a small portion of the anatomy—such as the hand. The direct attachment of the surgical table to the X-ray machine allows the surgeon to conveniently visualize the internal placement of orthopaedic hardware and other features both before and during the surgery.

REFERENCE NUMERALS IN THE DRAWINGS

| 10 | C-arm machine | 12 | base |
|----|---------------|----|------|
| 14 | main housing | 16 | sliding joint support |
| 18 | pivot joint | 20 | sliding joint |
| 22 | C-arm | 24 | emitter |
| 26 | image intensifier | 28 | mounting surface |
| 30 | C-arm support | 32 | surgical table |
| 34 | main plate | 36 | track |
| 38 | slider | 40 | jaw |
| 42 | locking lever | 44 | toggle slider |
| 46 | toggle lever | 48 | thrust link |
| 50 | gripping pad | 52 | cylindrical surface |
| 54 | conventional table | 56 | head support |
| 58 | spring clip | 60 | swivel slider |
| 62 | swivel jaw | 64 | lip |
| 66 | protrusion | | |

DESCRIPTION OF THE INVENTION

FIG. 1 shows prior art C-arm machine 10. It is generally used to X-ray specific regions of a patient's anatomy. Base 12 is provided with castors which allow the machine to be rolled into a desired location. Pivot joint 18 can be rotated to angularly displace the plane in which C-arm 22 resides. Sliding joint 20 can be unlocked to allow C-arm 22 to slide along the arc of its curvature. Thus, C-arm 22 is ultimately adjustable in roll and pitch.

C-arm 22 structurally mounts emitter 24 and image intensifier 26. Emitter 24 controllably emits a stream of X-rays toward image intensifier 26. Image intensifier 26 receives the stream of X-rays and enhances them for visualization, which is typically accomplished through a computer monitor. The anatomical features to be X-rayed must generally be placed proximate a line drawn between emitter 24 and image intensifier 26.

Many types of C-arm machines are in common use. The relative location of the emitter and image intensifier may be reversed on some machines. The mounting and positioning features of other machines are also different from the one shown in FIG. 1. The present invention is suitable for use with a wide variety of machines, and should not be viewed as limited to any one particular type.

Figure 2:
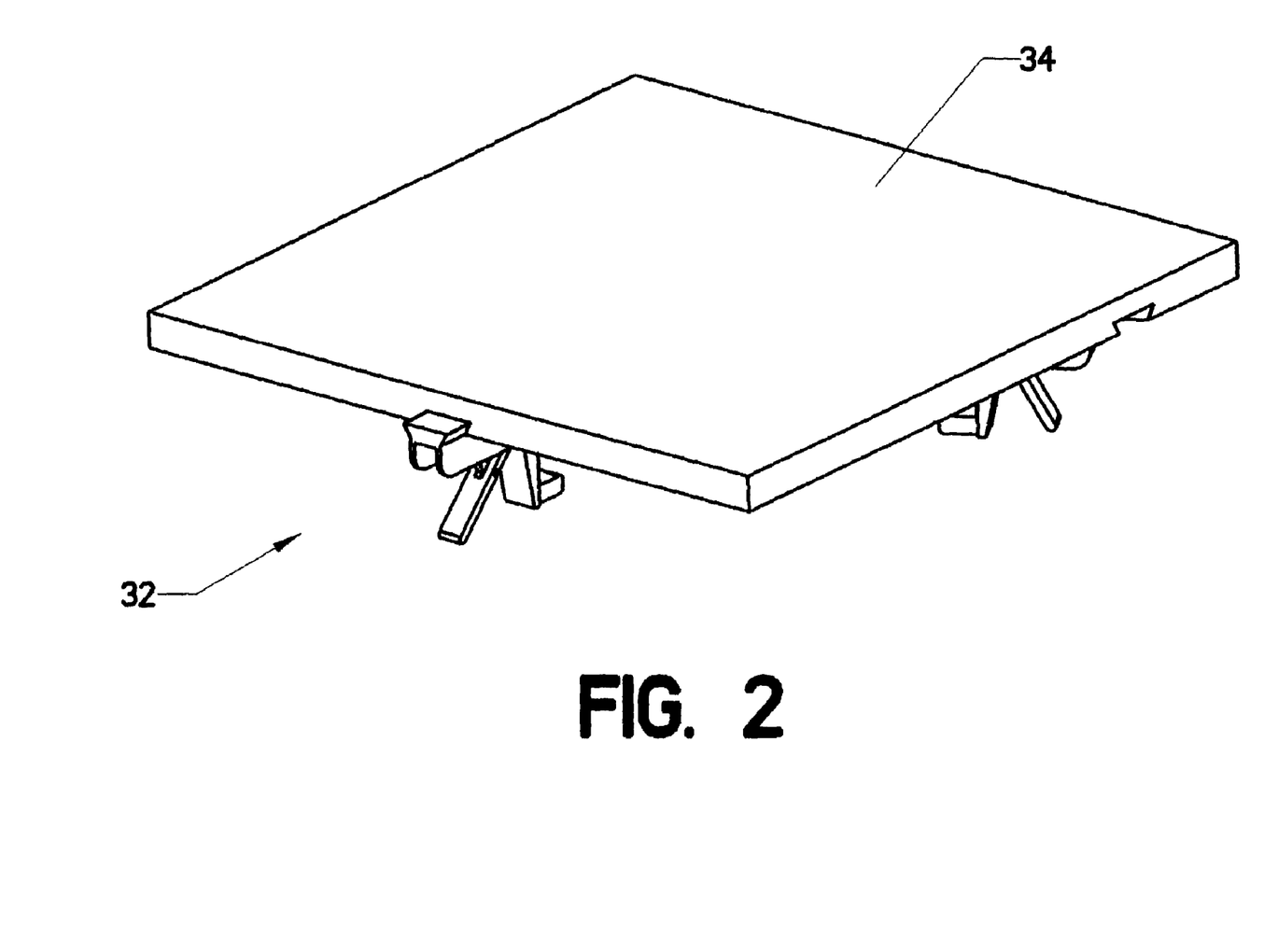
FIG. 2 is an isometric view, showing the present invention.
Figure 3:
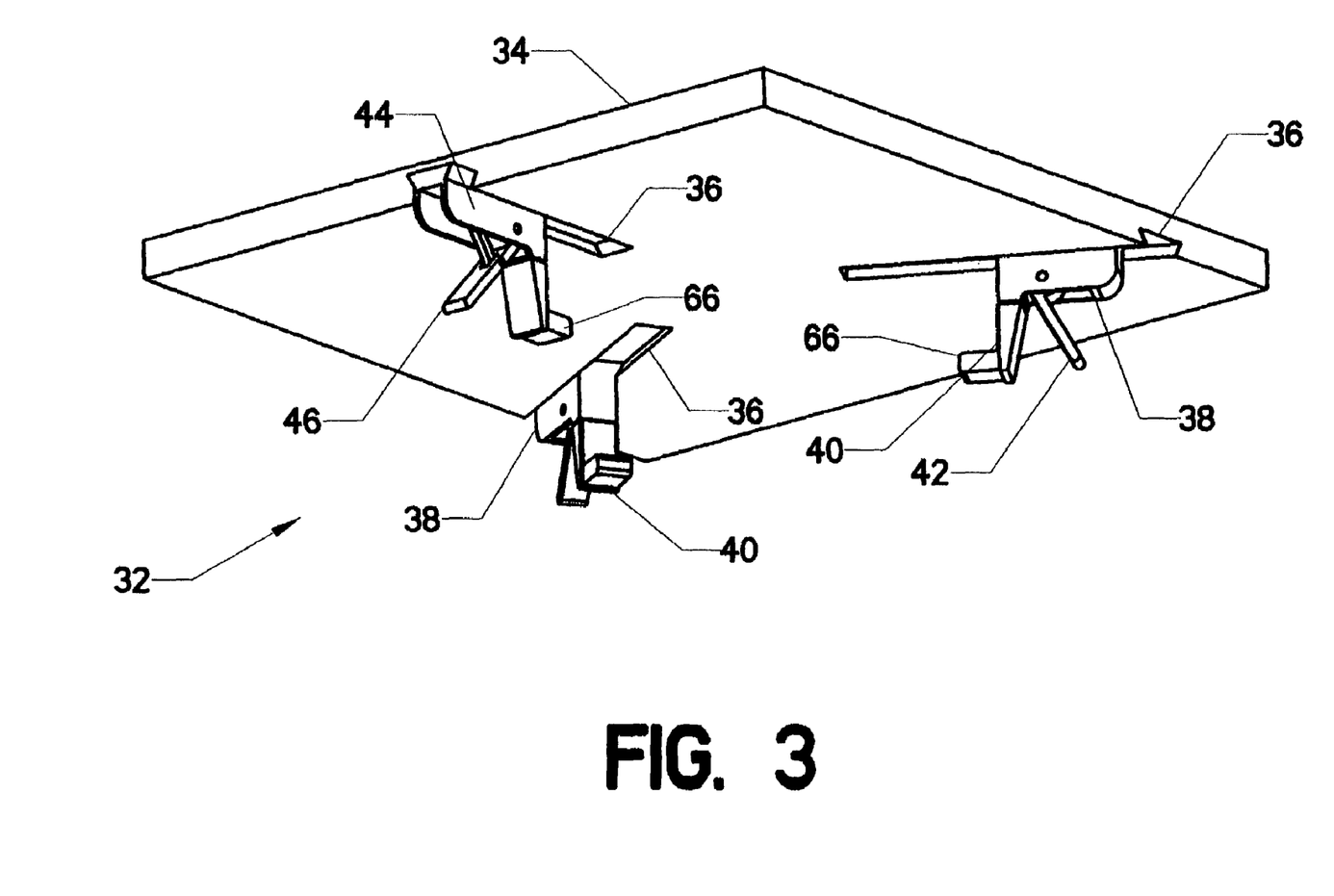
FIG. 3 is an isometric view, showing the present invention from a different perspective.

FIG. 2 shows the present invention. Main plate 34 is its primary structural component. The upper surface of main plate 34 serves as a surgical site. The lower surface contains mounting features. Main plate 34 is made of a material which allows the free transmission of X-rays with minimal absorption or distortion. FIG. 3 shows the lower side of the invention. Three tracks 36 are provided. These tracks are angularly displaced in 120 degree increments, with the outer extreme of each track being proximate an edge of main plate 34 and the inner extreme of each track being proximate the center of main plate 34.

Two tracks are equipped with sliders 38. Each slider 38 has a jaw 40 and a locking lever 42. Each slider 38 is free to slide within its track 36 until its locking lever 42 is pulled downward, at which point the locking lever 42 toggles into a locked position and locks the slider 38 in its track 36. The third track 36 is occupied by toggle slider 44. Toggle slider 44 is likewise free to slide within its track until toggle lever 46 is pressed upward.

Figure 4:
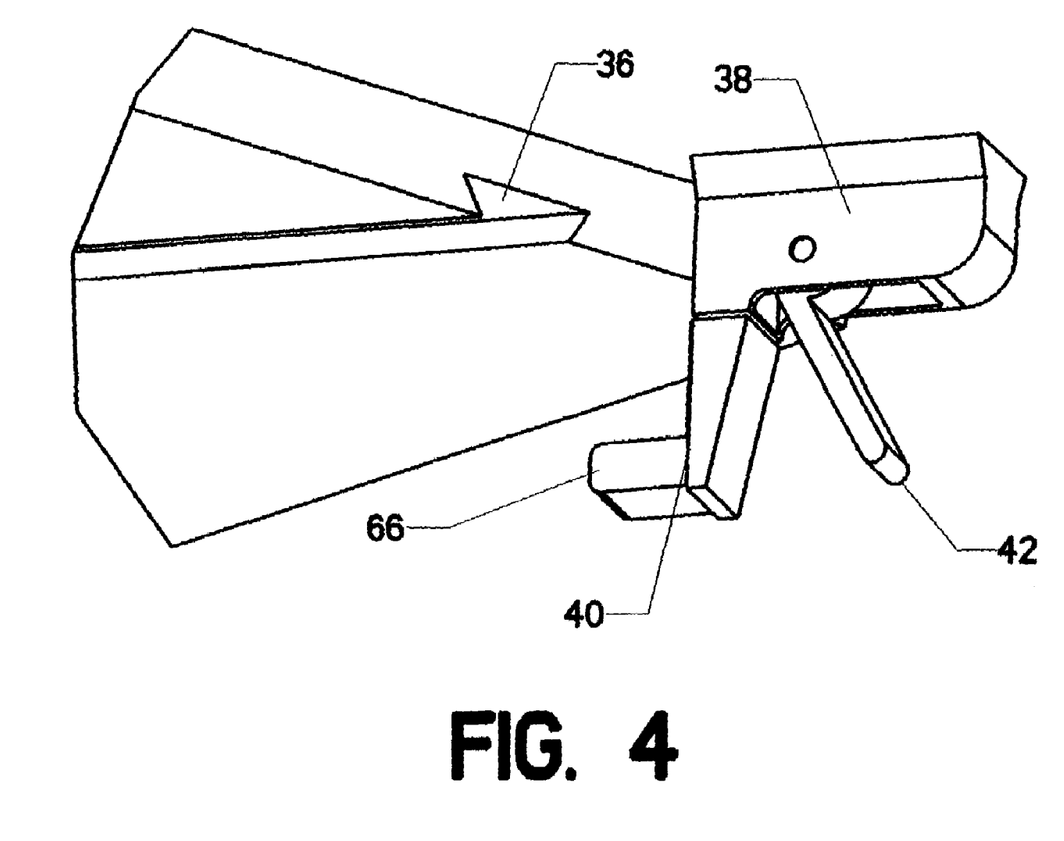
FIG. 4 is an isometric detail view, showing the features attaching the invention to the X-ray machine.

FIG. 4 shows track 36 and slider 38 in greater detail. The reader will observe that track 36 is cut in the shape of a dovetail—as is the upper portion of slider 38. Track 36 also exits an edge of main plate 34. This allows slider 38 to be easily removed from main plate 34 for sterilization or other purposes. Jaw 40 descends from slider 38. This feature is intended to actually engage a portion of the X-ray machine. Locking lever 42 is pivotally mounted to slider 38. When it is rotated downward, slider 38 is locked in position within track 36. A variety of mechanisms can be employed to achieve this function. Other features could also be substituted for locking lever 42. As such mechanical locking features are well known, they have not been illustrated in detail.

The reader will observe the position and nature of protrusion 66. It is intended for use with a C-arm machine having a lip 64. For C-arm machines not having a lip 64, protrusion 66 can be omitted (as will be explained in more detail subsequently).

Figure 5:
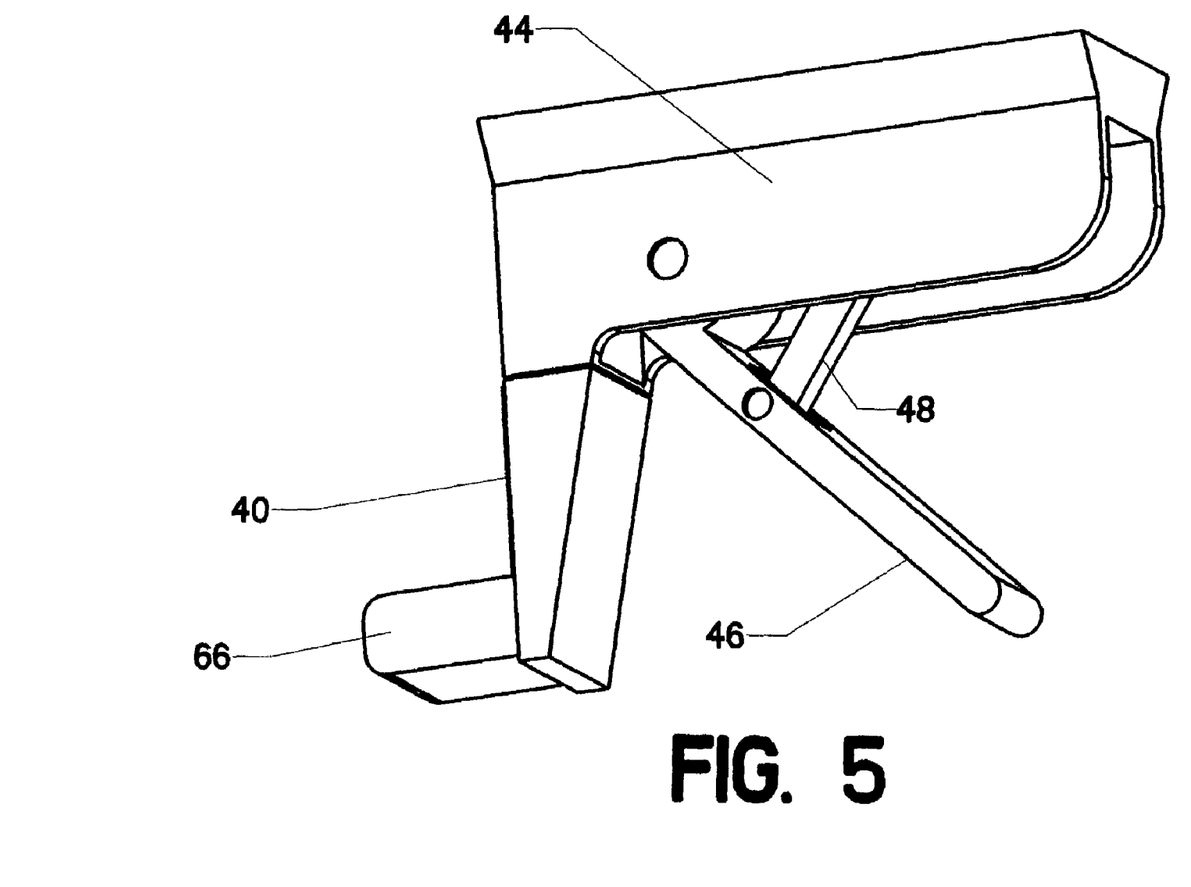
FIG. 5 is an isometric detail view, showing the features attaching the invention to the X-ray machine.

FIG. 5 shows toggle slider 44 in detail. Its upper portion is also formed in the shape of a dovetail in order to engage a track 36. Jaw 40 is identical to the one found on slider 38 (including the optional addition of a protrusion 66). Toggle lever 46 is pivotally mounted on toggle slider 44. Thrust link 48 is pivotally mounted on toggle lever 46 (to preferably form a classic "four bar" linkage). When toggle lever 46 is pushed upward, two things occur: (1) toggle slider 44 is initially stopped in its place within its track 38, and (2) The upper extreme of thrust link 48 bears against main plate 34 and thrusts toggle slider 44 slightly forward (to the left in the view as shown). This action provides significant clamping force, as will be explained subsequently.

Figure 6:
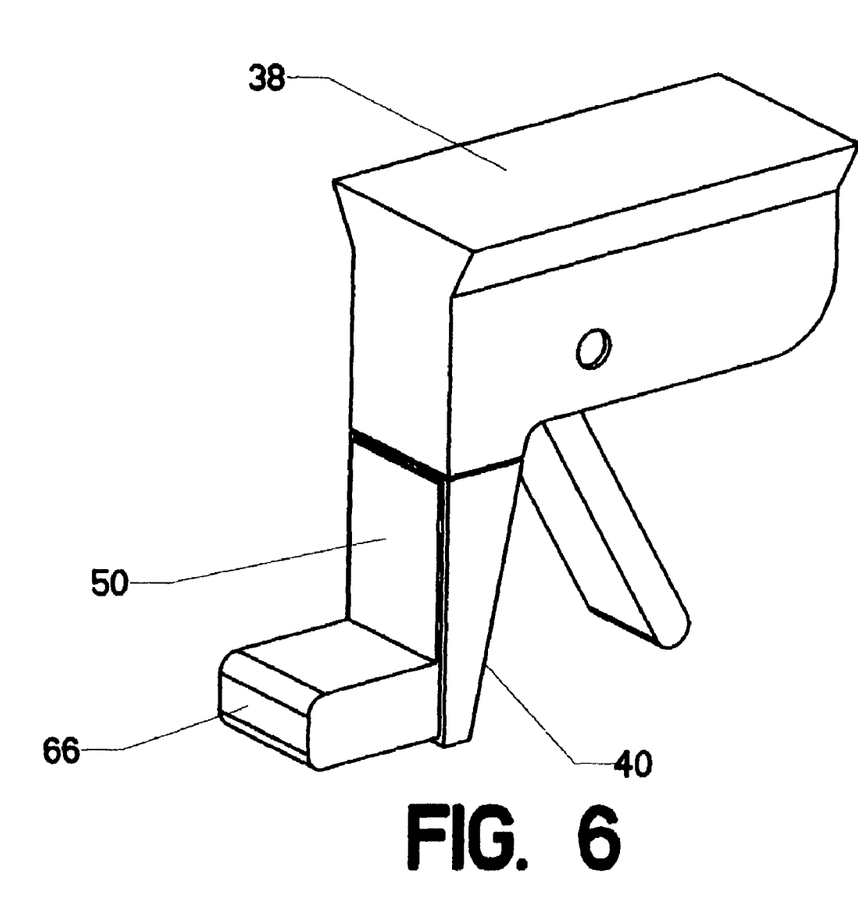
FIG. 6 is an isometric detail view, showing the features attaching the invention to the X-ray machine.
Figure 7:
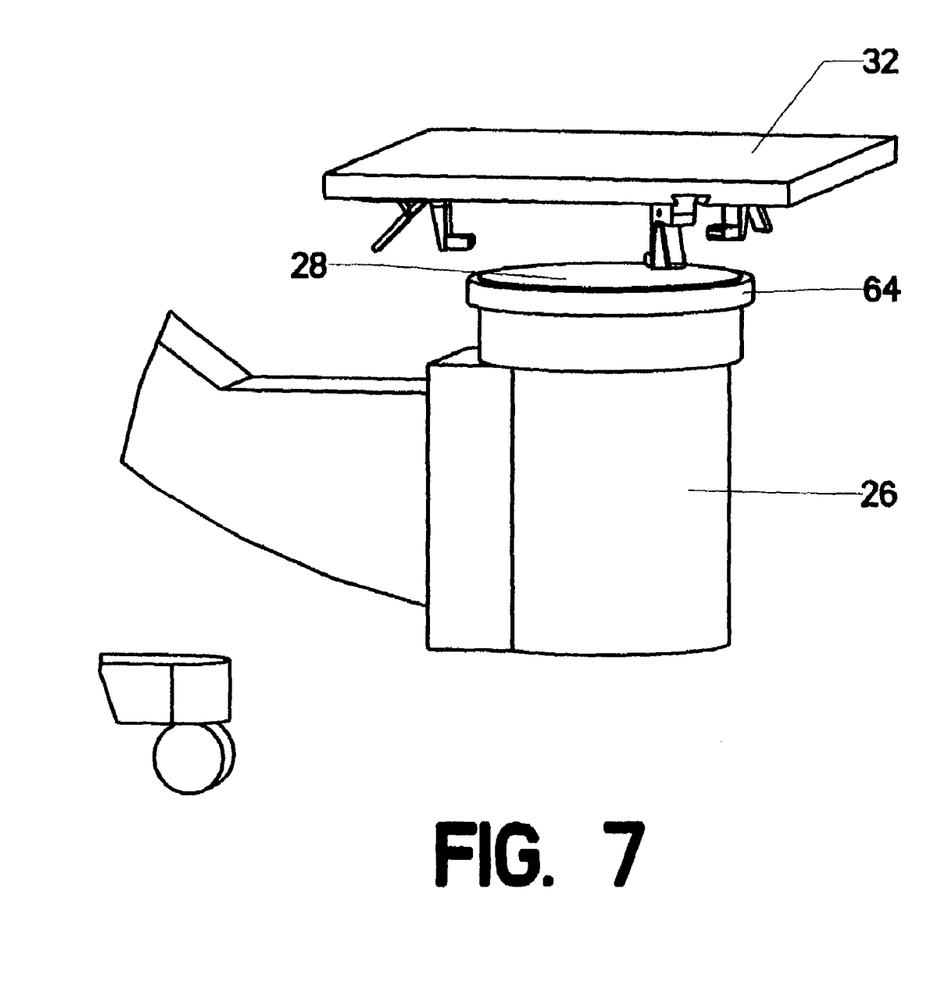
FIG. 7 is an isometric view, showing the attachment of the invention to an X-ray machine.

FIG. 6 shows slider 38 from another perspective. Gripping pad 50—made of a resilient material—is preferably placed on the inward facing surface of jaw 40 in order to prevent marring a surface against which jaw 40 rests. If a protrusion 66 is included, it is likewise given a non-marring face.

The installation and use of the invention are explained in FIGS. 7 through 10. The invention is typically installed on the image intensifier of a C-arm X-ray machine In FIG. 7, surgical table 32 is shown near image intensifier 26. It is preferably mounted directly over mounting surface 28. It should be mounted very nearly parallel with mounting surface 28 in order to provide the best possible X-ray images.

Figure 8:
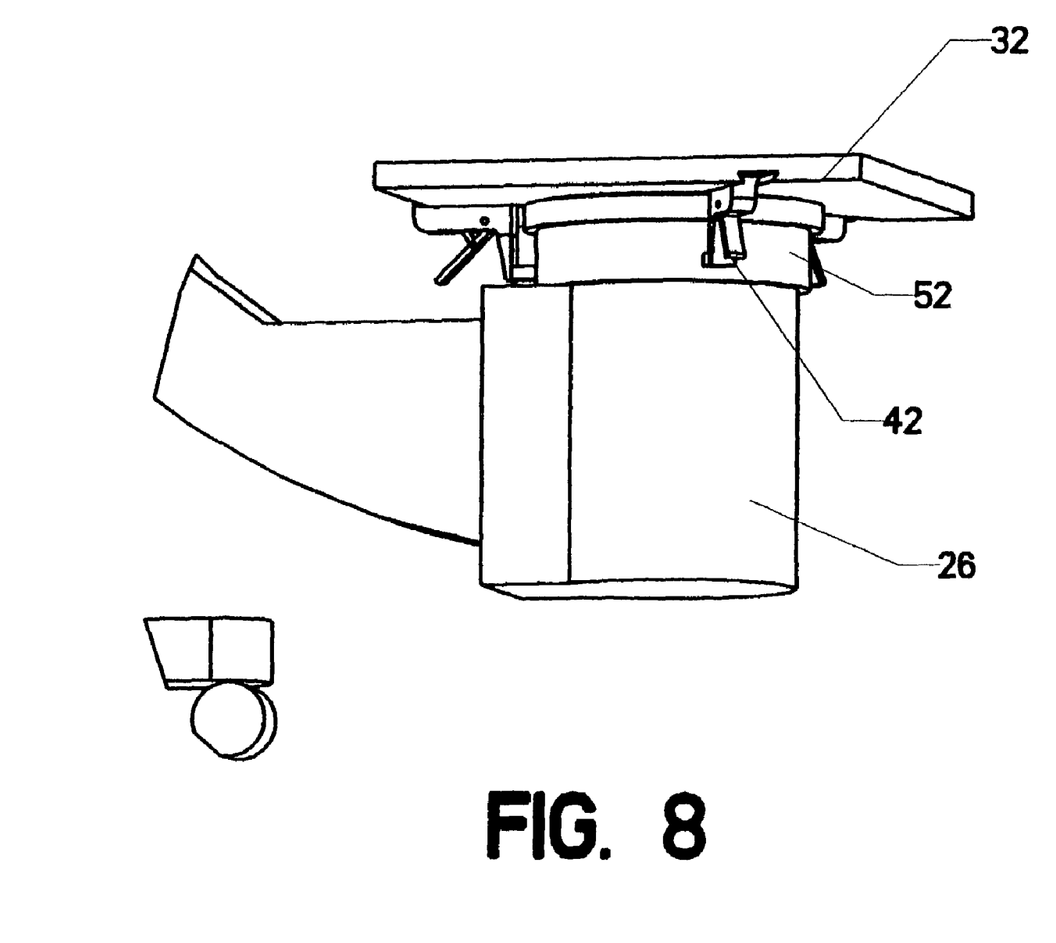
FIG. 8 is an isometric view, showing the attachment of the invention to an X-ray machine.

The user typically retracts the two sliders 38 and toggle slider 44 to positions near the edges of main plate 34. Main plate 34 is then placed atop mounting surface 28, as shown in FIG. 8. Main plate 34 is maneuvered into a desired position. The two sliders 38 are then pushed forward in their respective tracks 36 until the two jaws 40 rest against cylindrical surface 52. The two locking levers 42 are then rotated downward to lock the two sliders 38 in position.

In the case of a C-arm machine having a lip 64 (the version actually shown in the drawings), the mechanical interface will be different. The jaws 40 actually clear the outer perimeter of lip 64. Protrusions 66 then actually bear against cylindrical surface 52.

Figure 9:
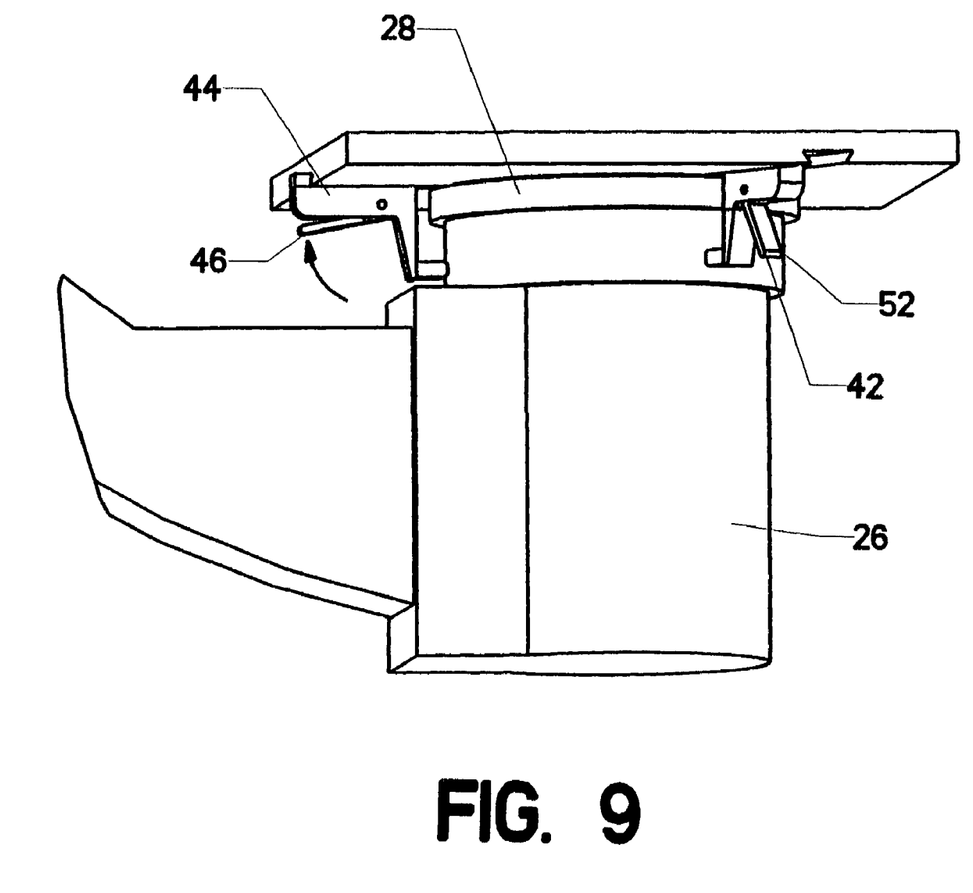
FIG. 9 is an isometric view, showing the attachment of the invention to an X-ray machine.

Turning now to FIG. 9—toggle slider 44 is advanced until its jaw 40 (or protrusion 66, in the case of a machine having a lip) likewise rests against cylindrical surface 52. Toggle lever 46 is then rotated upward as shown. This action pushes toggle slider 44 forward with respect to its track and then locks it in place (such as by the action of toggling a four bar linkage over center or other known mechanical means). Thus, the three jaws 40 (or protrusions 66) are drawn tightly against cylindrical surface 52, thereby affixing main plate 34 atop mounting surface 28.

The result is a small surgical table affixed directly to the C-arm machine. This allows the surgeon to perform surgical procedures directly over the X-ray image intensifier. Accurate X-ray visualization of the anatomy proximate the surgical site is therefore enhanced.

Figure 10:
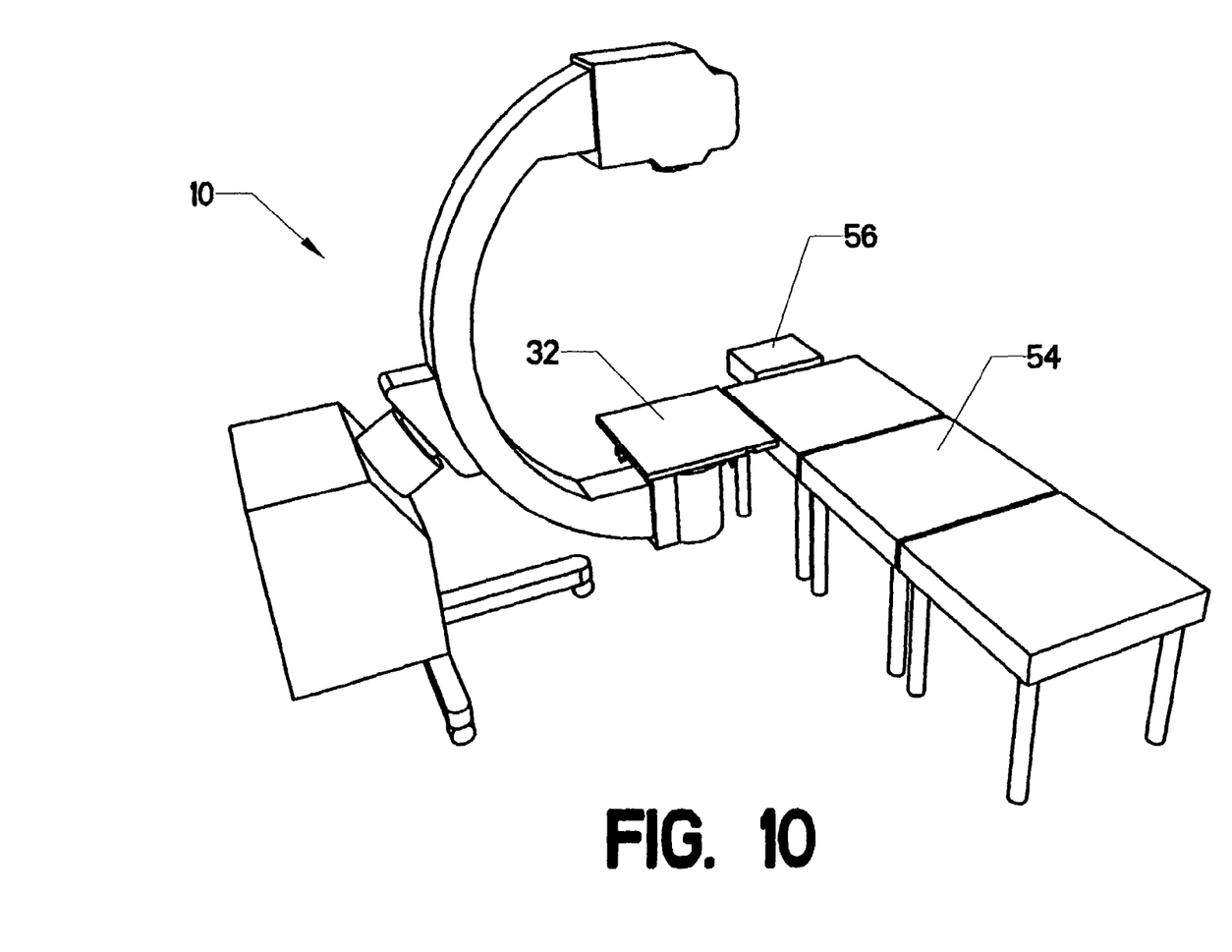
FIG. 10 is an isometric view, showing the invention configured for use.

Surgical table 32 is preferably used in conjunction with prior art devices for holding the patient in position. FIG. 10 shows one possible configuration. C-arm machine 10 with attached surgical table 32 is placed next to conventional table 54 with head support 56. The patient is placed face-up on conventional table 54. The patient's right arm would then be extended out to the patient's right, where the patient's hand/wrist area could be secured to surgical table 32. The surgeon would then perform a procedure on the patient's hand while it remains affixed to surgical table 32.

As one example—the surgeon may need to place orthopaedic hardware in the patient's hand to repair a fracture. X-ray images can be taken before, during, and after the placement of the hardware to ensure the surgeon's satisfaction with the placement.

Figure 11:
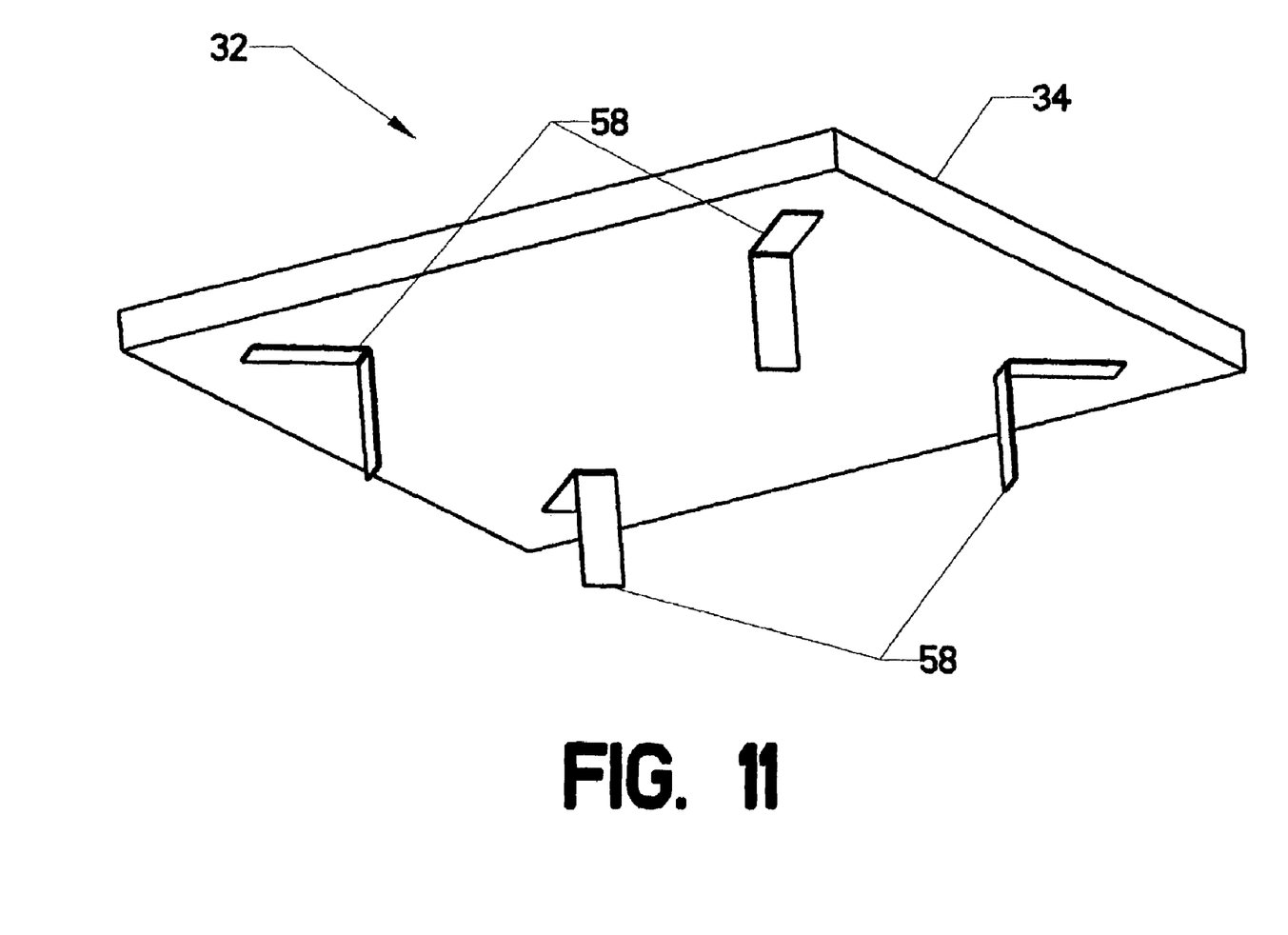
FIG. 11 is an isometric view, showing an alternate embodiment of the invention.

The adjustable features shown on surgical table 32 allow its use with a variety of different machines. Much simpler hardware can be used to attach the table to a particular type of machine. FIG. 11 shows main plate 34 with four descending resilient spring clips 58. These are fixed in place for use with an image intensifier having a known diameter. The elastic nature of these spring clips 58 allow them to grip cylindrical surface 52 on image intensifier 26 and hold surgical table 32 in place. Simpler fastening hardware can also be employed if the modification of the X-ray machine is allowed (such as screws, screw clamps, and the like).

Figure 12:
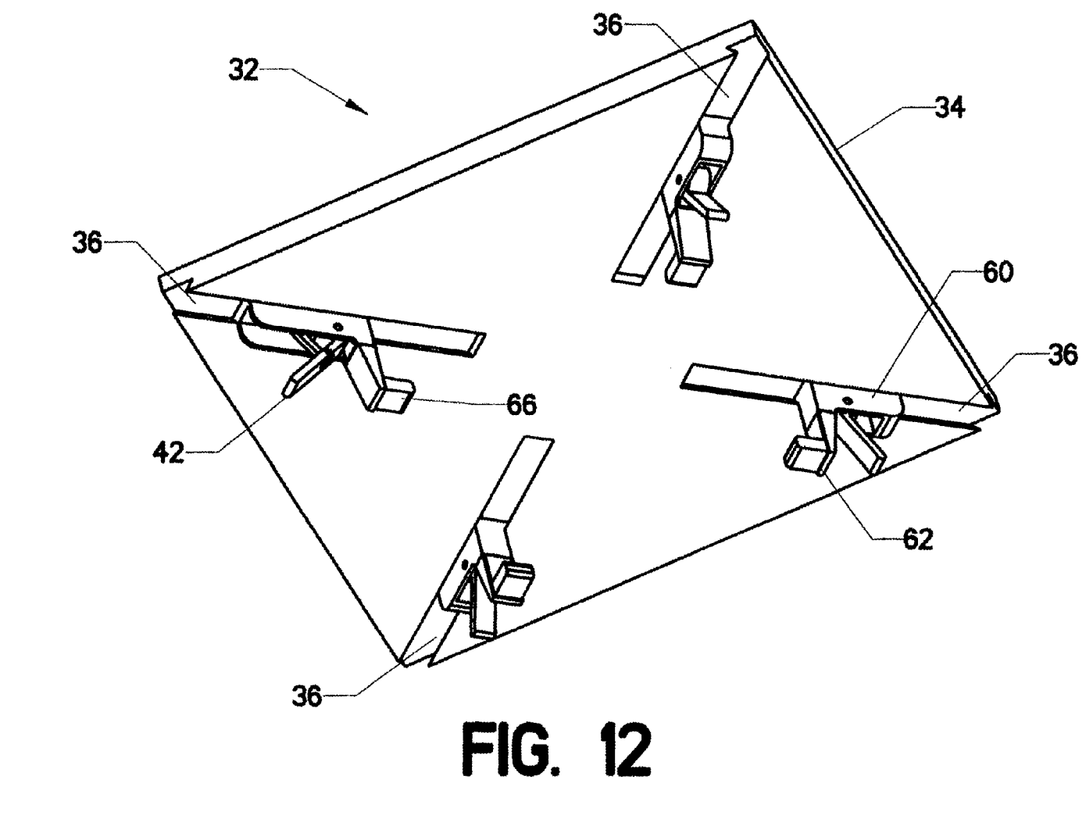
FIG. 12 is an isometric view, showing an alternate embodiment of the invention.

It is also possible to attach the surgical table to the X-ray emitter rather than the image intensifier. Returning briefly to FIG. 1, the reader will observe that emitter 24 assumes a generally rectangular shape. The three jaw clamping system depicted in FIG. 3 is ill suited for mounting on this geometry. FIG. 12 shows a second alternate embodiment configured for mounting on an emitter. Four jaws are used instead of three. Four swivel slider 60 each adjustably slide within four tracks 36. Each swivel slider 60 has a pivotally mounted swivel jaw 62. Swivel jaws 62 are capable of swiveling to bear against irregular surfaces when the fourth swivel sliders 60 are advanced to lock main plate 34 in position over an emitter. Four locking levers 42 are provided to lock the swivel sliders in position. One or more toggle levers may also be provided to give added clamping force. As for the prior examples, protrusions 66 can be added for each of the swivel jaws 62 in order to accommodate the presence of a lip on the C-arm machine.

The preceding description contains significant detail regarding the novel aspects of the present invention. It is should not be construed, however, as limiting the scope of the invention but rather as providing illustrations of the preferred embodiments of the invention. Thus, the scope of the invention should be fixed by the following claims, rather than by the examples given.

Having described my invention, I claim:

1. A surgical table configured for attachment to an X-ray machine, wherein said X-ray machine has an image intensifier which receives X-rays in a direction approximately transverse to a mounting surface, comprising:
   a. a main plate, having an upper surface and a lower surface, made from a material which allows X-rays to pass therethrough with minimal absorption or distortion;
   b. an attachment means, affixed to said main plate and configured to attach said main plate to said image intensifier in an orientation wherein said lower surface is proximate to and parallel to said mounting surface and said upper surface is available for use as a surgical site; and
   c. wherein said attachment means are adjustable in order to allow the attachment of said surgical table to a variety of said X-ray machines, wherein said attachment means includes
      i. a first slider, slidably movable along said lower surface of said main plate from a first position proximate an edge of said main plate to a second position proximate the center of said main plate;
      ii. a first locking means for locking said first slider in a desired position;
      iii. a second slider, slidably movable along said lower surface of said main plate from a first position proximate an edge of said main plate to a second position proximate the center of said main plate; and
      iv. a second locking means for locking said second slider in a desired position, such that said image intensifier is clamped between said first and second sliders, thereby attaching said surgical table to said image intensifier.

2. A surgical table as recited in claim 1, wherein said attachment means further comprises:
   a. a third slider, slidably movable along said lower surface of said main plate from a first position proximate an edge of said main plate to a second position proximate the center of said main plate; and
   b. a third locking means for locking said third slider in a desired position, such that said image intensifier is clamped between said first, second, and third sliders, thereby attaching said surgical table to said image intensifier.

3. A surgical table as recited in claim 2, wherein:
   a. said first slider has a swivel jaw descending from and rotatably attached thereto;
   b. said second slider has a swivel jaw descending from and rotatably attached thereto; and
   c. said third slider has a swivel jaw descending from and rotatably attached thereto.

4. A surgical table as recited in claim 1, wherein said attachment means further comprises:
   a. a third slider, slidably movable along said lower surface of said main plate from a first position proximate an edge of said main plate to a second position proximate the center of said main plate;
   b. a third locking means for locking said third slider in a desired position,
   c. a fourth slider, slidably movable along said lower surface of said main plate from a first position proximate an edge of said main plate to a second position proximate the center of said main plate; and
   d. a fourth locking means, such that said image intensifier is clamped between said first, second, third, and fourth sliders, thereby attaching said surgical table to said image intensifier.

5. A surgical table as recited in claim 4, wherein:
   a. said first slider has a swivel jaw descending from and rotatably attached thereto;
   b. said second slider has a swivel jaw descending from and rotatably attached thereto;
   c. said third slider has a swivel jaw descending from and rotatably attached thereto; and
   d. said fourth slider has a swivel jaw descending from and rotatably attached thereto.

6. A surgical table configured for attachment to an X-ray machine, wherein said X-ray machine has an image intensifier which receives X-rays in a direction approximately transverse to a mounting surface, comprising:
   a. a main plate, having an upper surface and a lower surface, made from a material which allows X-rays to pass therethrough with minimal absorption or distortion;
   b. an attachment means, affixed to said main plate and configured to attach said main plate to said image intensifier in an orientation wherein said lower surface is proximate to and parallel to said mounting surface and said upper surface is available for use as a surgical site; and
   c. wherein said attachment means comprises a first spring clip descending from said main plate, a second spring clip descending from said main plate, and a third spring clip descending from said main plate, wherein said first, second, and third spring clips are configured to bear against said image intensifier, thereby attaching said surgical table to said image intensifier.

7. A surgical table configured for attachment to an X-ray machine, wherein said X-ray machine has an emitter which transmits X-rays in a direction approximately transverse to a mounting surface, comprising:
   a. a main plate, having an upper surface and a lower surface, made from a material which allows X-rays to pass therethrough with minimal absorption or distortion;
   b. attachment means, affixed to said main plate and configured to attach said main plate to said emitter in an orientation wherein said lower surface is proximate to and parallel to said mounting surface and said upper surface is available for use as a surgical site; and
   c. wherein said attachment means includes
      i. a first slider, slidably movable along said lower surface of said lower surface of said main plate from a first position proximate an edge of said main plate to a second position proximate the center of said main plate;
      ii. a first locking means for locking said first slider in a desired position;

iii. a second slider, slidably movable along said lower surface of said main plate from a first position proximate an edge of said main plate to a second position proximate the center of said main plate; and iv. a second locking means for locking said second slider in a desired position, such that said emitter is clamped between said first and second sliders, thereby attaching said surgical table to said emitter.

8. A surgical table as recited in claim 7, wherein said attachment means further comprises:

a. a third slider, slidably movable along said lower surface of said main plate from a first position proximate an edge of said main plate to a second position proximate the center of said main plate; and b. a third locking means for locking said third slider in a desired position, such that said emitter is clamped between said first, second, and third sliders, thereby attaching said surgical table to said emitter.

9. A surgical table as recited in claim 8, wherein:

a. said first slider has a swivel jaw descending from and rotatably attached thereto;

b. said second slider has a swivel jaw descending from and rotatably attached thereto; and c. said third slider has a swivel jaw descending from and rotatably attached thereto.

10. A surgical table as recited in claim 7, wherein said attachment means further comprises:

a. a third slider, slidably movable along said lower surface of said main plate from a first position proximate an edge of said main plate to a second position proximate the center of said main plate;

b. a third locking means for locking said third slider in a desired position;

c. a fourth slider, slidably movable along said lower surface of said main plate from a first position proximate an edge of said main plate to a second position proximate the center of said main plate; and d. a fourth locking means, such that said emitter is clamped between said first, second, third, and fourth sliders, thereby attaching said surgical table to said emitter.

11. A surgical table as recited in claim 9, wherein:

a. said first slider has a swivel jaw descending from and rotatably attached thereto;

b. said second slider has a swivel jaw descending from and rotatably attached thereto;

c. said third slider has a swivel jaw descending from and rotatably attached thereto; and d. said fourth slider has a swivel jaw descending from and rotatably attached thereto.

12. A surgical table configured for attachment to an X-ray machine, wherein said X-ray machine has an emitter which transmits X-rays in a direction approximately transverse to a mounting surface, comprising:

a. a main plate, having an upper surface and a lower surface, made from a material which allows X-rays to pass therethrough with minimal absorption or distortion;

b. attachment means, affixed to said main plate and configured to attach said main plate to said emitter in an orientation wherein said lower surface is proximate to and parallel to said mounting surface and said upper surface is available for use as a surgical site; and c. wherein said attachment means comprises a first spring clip descending from said main plate, a second spring clip descending from said main plate, and a third spring clip descending from said main plate, wherein said first, second, and third spring clips are configured to bear against said emitter, thereby attaching said surgical table to said emitter.

\* \* \* \* \*